United States Patent [19]
Bhattacharya et al.

[11] Patent Number: 5,659,017
[45] Date of Patent: Aug. 19, 1997

[54] ANION EXCHANGE PROCESS FOR THE PURIFICATION OF FACTOR VIII

[75] Inventors: Prabir Bhattacharya, Walnut; Toshiharu Motokubota, Arcadia; Norman M. Fedalizo, Rowland Heights, all of Calif.

[73] Assignee: Alpha Therapeutic Corporation, Los Angeles, Calif.

[21] Appl. No.: 554,724

[22] Filed: Nov. 7, 1995

[51] Int. Cl.$^6$ ................................................ C07K 14/755
[52] U.S. Cl. ........................................................ 530/383
[58] Field of Search ............................. 530/383; 514/612

[56] References Cited

U.S. PATENT DOCUMENTS

| Re. 29,798 | 10/1978 | Johnson . | |
|---|---|---|---|
| Re. 32,011 | 10/1985 | Zimmerman et al. | 260/112 B |
| 3,560,475 | 2/1971 | Fekete et al. | 260/112 |
| 3,631,018 | 12/1971 | Shanbrom et al. | 260/112 B |
| 3,682,881 | 8/1972 | Fekete et al. | 260/112 B |
| 3,770,631 | 11/1973 | Fekete et al. | 210/53 |
| 3,803,115 | 4/1974 | Fekete et al. | 260/112 B |
| 3,839,314 | 10/1974 | Fekete et al. | 260/112 B |
| 3,893,990 | 7/1975 | Fekete et al. | 260/112 B |
| 3,893,991 | 7/1975 | Fekete et al. | 260/112 B |
| 3,920,625 | 11/1975 | Anderson et al. | 260/112 B |
| 4,069,216 | 1/1978 | Shanbrom | 260/112 B |
| 4,089,944 | 5/1978 | Thomas | 424/101 |
| 4,093,608 | 6/1978 | Iga et al. | 260/112 B |
| 4,141,887 | 2/1979 | Seufert | 260/112 B |
| 4,170,590 | 10/1979 | Stephan et al. | 260/112 B |
| 4,188,318 | 2/1980 | Shanbrom | 260/112 B |
| 4,189,425 | 2/1980 | Shanbrom et al. | 260/112 B |
| 4,210,580 | 7/1980 | Amrani | 260/112 B |
| 4,272,523 | 6/1981 | Kotitschke et al. | 424/101 |
| 4,278,594 | 7/1981 | Amrani | 260/112 B |
| 4,305,870 | 12/1981 | Liu et al. | 260/112 B |
| 4,314,997 | 2/1982 | Shanbrom | 424/101 |
| 4,315,919 | 2/1982 | Shanbrom | 424/177 |
| 4,348,315 | 9/1982 | Blombäck et al. | 260/112 B |
| 4,382,028 | 5/1983 | Paget | 260/112 B |
| 4,383,989 | 5/1983 | Rock | 124/101 |
| 4,404,131 | 9/1983 | Schwarz et al. | 260/112 B |
| 4,455,301 | 6/1984 | Mitra et al. | 424/101 |
| 4,456,590 | 6/1984 | Rubinstein | 424/101 |
| 4,495,175 | 1/1985 | Chavin et aql. | 424/101 |
| 4,508,709 | 4/1985 | Amphlett et al. | 424/101 |
| 4,543,210 | 9/1985 | Mitra et al. | 260/112 B |
| 4,556,558 | 12/1985 | Rubinstein | 424/101 |
| 4,578,218 | 3/1986 | Saundry et al. | 260/112 B |
| 4,650,858 | 3/1987 | Rasmussen et al. | 530/383 |
| 4,673,733 | 6/1987 | Chandra et al. | 530/344 |
| 4,675,385 | 6/1987 | Herring | 530/383 |
| 4,710,381 | 12/1987 | Kunicki et al. | 424/101 |
| 4,739,039 | 4/1988 | Vasquez et al. | 530/383 |
| 4,743,680 | 5/1988 | Mathews et al. | 530/383 |
| 4,822,872 | 4/1989 | Kameyama et al. | 530/383 |
| 4,845,074 | 7/1989 | Rubinstein | 514/2 |
| 4,847,362 | 7/1989 | Mathews et al. | 530/383 |
| 4,952,675 | 8/1990 | Mathews et al. | 530/383 |
| 4,970,300 | 11/1990 | Fulton et al. | 530/383 |
| 4,994,438 | 2/1991 | Rubinstein | 514/2 |
| 5,043,428 | 8/1991 | Heimburger et al. | 530/383 |
| 5,097,018 | 3/1992 | Rubinstein | 530/383 |
| 5,099,002 | 3/1992 | Rubinstein | 530/381 |
| 5,110,907 | 5/1992 | Kosow et al. | 530/383 |
| 5,118,614 | 6/1992 | Rybák et al. | 435/13 |
| 5,118,795 | 6/1992 | Rubinstein | 530/383 |
| 5,138,034 | 8/1992 | Uemura et al. | 530/413 |
| 5,177,191 | 1/1993 | Brockway et al. | 530/383 |
| 5,245,014 | 9/1993 | Kaersgaard | 530/383 |
| 5,252,709 | 10/1993 | Burnouf et al. | 530/382 |
| 5,252,710 | 10/1993 | Dazey et al. | 530/383 |
| 5,259,951 | 11/1993 | Arrighi et al. | 210/660 |
| 5,278,289 | 1/1994 | Johnson et al. | 530/383 |
| 5,288,853 | 2/1994 | Bhattacharva et al. | 530/383 |
| 5,356,878 | 10/1994 | Brockway et al. | 514/21 |
| 5,371,195 | 12/1994 | Grandgeorge et al. | 530/383 |
| 5,399,670 | 3/1995 | Bhattacharya et al. | 530/383 |
| 5,408,039 | 4/1995 | Burnouf-Radosevich et al. | 530/383 |
| 5,410,022 | 4/1995 | Eibl et al. | 530/383 |
| 5,424,401 | 6/1995 | Heimburger et al. | 530/383 |
| 5,451,662 | 9/1995 | Naveh et al. | 530/351 |
| 5,470,954 | 11/1995 | Neslund et al. | 530/383 |
| 5,484,890 | 1/1996 | Johnson et al. | 530/383 |

FOREIGN PATENT DOCUMENTS 1222810   2/1971   United Kingdom .

OTHER PUBLICATIONS

Arrighi et al., "Factor VIII:c Concentrate Virus Inactivated: Progress in Purification by Using Classic Chromatographic Methods," *Vox Sang* 64:13–18 (1993).

Bihoreau et al., "Copper–Atom Identification in the Active and Inactive Forms of Plasma–Derived FVIII and Recombinant FVIII–ΔII," *Eur. J. Biochem.* 220:41–48.

Friesen, "Chromatographic Methods of Fractionation," *Develop. Biol. Standard.* 67:3–13 (1987).

Hershgold, "Discussion Paper: Factor VIII," *Ann. N.Y. Acad. Sci.* 240:70–3 (Jan. 20, 1975).

Lemon et al., "Removal/Neutralization of Hepatitis A Virus During Manufacture of High Purity, Solvent/Detergent Factor VIII Concentrate," *Journal of Medical Virology* 43:44–49 (1994).

Pharmacia LKB Biotechnology, "Ion Exchange Chromatography," 3rd edition (18–1022–19), pp. 5–10.

(List continued on next page.)

*Primary Examiner*—Howard E. Schain
*Attorney, Agent, or Firm*—Christie, Parker & Hale, LLP

[57] ABSTRACT

A new method for purifying Factor VIII complex from an impure protein fraction, usually cryoprecipitate, is disclosed. The cryoprecipitate is dissolved in a heparin solution. Then Factor VIII complex is initially purified by polyethylene glycol precipitation. The Factor VIII containing supernatant collected after the precipitation is loaded into an anion exchange column that has a quaternary amino ethyl group. The Factor VIII complex is then eluted from the column with a buffer comprising from about 0.14M to about 0.20M $CaCl_2$. The final step in the purification is to precipitate the Factor VIII complex in the presence of glycine and sodium chloride. The precipitated Factor VIII complex is then reconstituted and stabilized. The reconstituted Factor VIII complex can then be lyophilized and dry heated to obtain a final Factor VIII product.

23 Claims, 8 Drawing Sheets

OTHER PUBLICATIONS

Schwarz et al., "Removal of Parvovirus B19 from Contaminated Factor VIII During Fractionation," *Journal of Medical Virology* 35:28–31 (1991).

Schwinn et al., "Progress in Purification of Virus–Inactivated Factor VIII Concentrates," *Arzneim.–Forsh./Drug Res.* 39(II):1302–1305 (1989).

Schwinn et al., "A Solvent I Detergent Treated, Pasteurized and Highly Purified Factor VIII Concentrate," *Arzneim.–Forsh./Drug Res.* 44(I):188–191 (1994).

TosoHaas, "Editorial—Ion Exchange Process", *The Peak—A ToSoHaas Newsletter*, vol. 3, Issue 1, pp. 1–2.

TosoHaas, "Toyopearl® Chromatographic Resins" brochure, pp. 1–7.

Zhang et al., "Role of the Hexapeptide Disulfide Loop Present in the γ–Carboxyglutamic Acid Domain of Human Protein C in Its Activation Properties and in the in Vitro Anticoagulant Activity of Activated Protein C," *Biochemistry* 30:6696–6704 (1991).

ANION EXCHANGE PROCESS FOR THE PURIFICATION OF FACTOR VIII

FIELD OF THE INVENTION

The present invention relates to a method of purifying proteins using ion exchange chromatography. More specifically, the invention is directed to a process of using anion exchange chromatography to purify impure samples of Factor VIII complex.

BACKGROUND OF THE INVENTION

When a blood vessel is cut or ruptured, hemostasis (prevention of blood loss) is accomplished by several means including vascular spasm, formation of a platelet plug, blood coagulation, and growth of fibrous tissue into the blood clot. The process of hemostasis begins instantaneously after a blood vessel's integrity is compromised when the wall of the vessel contracts, thereby reducing the flow of blood from the ruptured vessel. Platelets then adhere to the end of the blood vessel, and after the platelets agglutinate, fibrin appears at the end of the ruptured vessel. Finally, a fibrin clot forms that stops the flow of blood. Once a blood clot has formed, it becomes invaded by fibroblasts which form connective tissue all throughout the clot.

Many different substances affect blood coagulation or clotting. Unfortunately, many people suffer from defects in the blood clotting mechanism and need to be treated with various pharmaceutical preparations. The most common disorder is a deficiency in functional Factor VIII complex.

Factor VIII complex is well known and is a large molecular weight complex composed of two different proteins, a carrier protein (von Willebrand Factor, vWF) and the procoagulant protein factor (Factor VIII:C). The two proteins are linked together by non-covalent bonds. Von Willebrand factor interacts with platelets in a way that promotes primary hemostasis.

The primary therapeutic use of Factor VIII complex has been its intravenous administration to hemophilia A patients. Hemophilia A is an inherited sex-linked coagulation disorder carried by females and expressed in males. In severe cases, relatively high concentration of Factor VIII complex are required to treat the hemophilia. These high concentrations are usually obtained by purification and concentration of Factor VIII complex from pools of human blood.

A Factor VIII complex product named Alphahate™, which is currently available from Alpha Therapeutic Corporation in Los Angeles, Calif., is a highly purified and processed Factor VIII complex that is prepared by means of a heparin affinity column. The method of purification is detailed in U.S. Pat. No. 5,288,853 to Bhattacharya et. al. issued on Feb. 22, 1994, which is hereby incorporated by reference. The Alphanate™ product is virus inactivated using methods including organic solvent detergent method. The specific activity of the Alphahate™ Factor VIII complex product which contains yon Willebrand factor (vWF) reached more than 100 U/mg of protein. However, using a heparin affinity column has the disadvantage in that the heparin resin has a low binding capacity for Factor VIII complex as well as a low specificity, which leads to low yields.

The technology of monoclonal antibodies has also been utilized for highly purified Factor VIII products, but the disadvantage of this method is the leaking of animal protein to the product. In addition, the cost of monoclonal antibodies is much higher than the conventional chromatography resin.

Currently, there is a need for an inexpensive new purification method using a column that has a high binding capacity for Factor VIII complex and also has a high specificity in order to obtain high yields.

SUMMARY OF THE INVENTION

The new method for purifying Factor VIII complex begins with the impure protein fraction, usually cryoprecipitate. The impure protein fraction is dissolved in a heparin solution. Then the Factor VIII complex is initially purified by polyethylene glycol ("PEG") precipitation. The Factor VIII containing supernatant is loaded into an anion exchange column containing a resin that incorporates quaternary amino ethyl (QAE) groups. The Factor VIII complex is eluted with a buffer comprising from about 0.14M to about 0.20M $CaCl_2$. The final step in the purification is to precipitate the Factor VIII complex in the presence of glycine and sodium chloride. The precipitated Factor VIII complex is then reconstituted and stabilized with a non-protein stabilizer. The reconstituted Factor VIII complex can then be lyophilized and dry heated to obtain a product ready for shipping.

The new purification method has several distinctive advantages over existing methods. One advantage is the use of a quaternary amino ethyl anion exchange resin which is less costly than the currently used resins. Another advantage is that the QAE resin has a much higher affinity for Factor VIII complex than currently used resins. The column volume can be reduced significantly from currently used resins due to the high binding capacity of the QAE resin. The overall recovery of Factor VIII is 80% more than that of the currently used heparin resin process. The specific activity of the new Factor VIII is 350 to 400 U/mg of protein, a much higher specific activity than currently available products on the market.

BRIEF DESCRIPTION OF THE DRAWINGS

Embodiments of the invention will now be described with reference to the following drawings wherein.

DESCRIPTION OF THE PREFERRED Embodiment

The process of this invention provides a simple and efficient purification method for high specific activity Factor VIII complex from an impure protein fraction. Previous methods for purifying Factor VIII, for example U.S. Pat. No. 5,288,853 issued to Bhattacharya et. al. on Feb. 22, 1994, the disclosure of which is hereby incorporated by reference, teach a process that is useful for purification of Factor VIII complex, but the prior art processes do not recover high amounts of Factor VIII complex from an impure protein fraction.

The phrase "impure protein fraction" as used herein means a solution which contains one or more protein(s) in addition to Factor VIII complex, where removal of these additional proteins is desired. The impure protein fraction used as the starting material for the purification of Factor VIII complex may be derived from a variety of sources, such as cryoprecipitate or other blood plasma-derived fractions, or it may be derived by recombinant-DNA or transgenic techniques.

Figure 1:
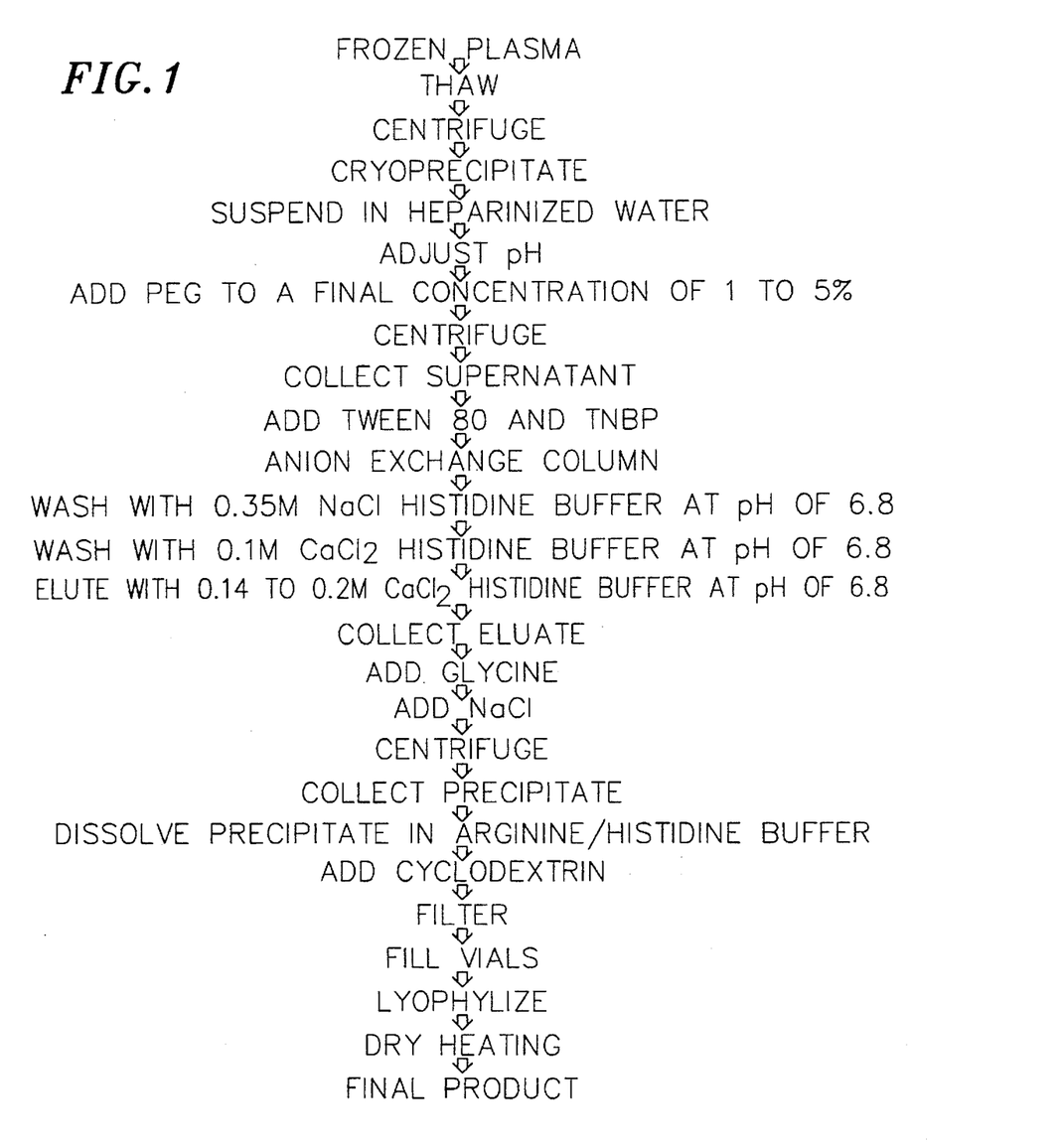
FIG. 1 is a flow diagram outlining the steps of the present invention.

The new method of purification is outlined in FIG. 1. Briefly, the new method for purifying Factor VIII complex begins with the impure protein fraction, usually cryoprecipitate. The Factor VIII complex contained in the impure protein fraction is initially purified by the addition of polyethylene glycol ("PEG") which precipitates mostly other proteins than Factor VIII complex. The supernatant which contains Factor VIII complex is loaded onto an anion exchange column using a binding buffer comprising 0.35M NaCl, 0.025M histidine, at a pH of 6.8. The Factor VIII complex is eluted with a buffer comprising from about 0.14M to about 0.2M $CaCl_2$, 0.025M histidine, at a pH of 6.8. The final step in the purification is to precipitate the Factor VIII complex in the presence of glycine and sodium chloride. The precipitated Factor VIII complex is then reconstituted in a solution of 0.1M arginine, 0.025M histidine, 3% wt/vol cyclodextrin, at a pH of 7.3. The Factor VIII solution is then sterile filtered to make a purified bulk solution of Factor VIII. The purified bulk can then be filled into vials at known Factor VIII concentrations, lyophilized, and dry heated at 80° C. for 72 hours to form the final product ready to be shipped to treating physicians and hospitals. A detailed description of the purification procedure is set out below.

Preparation of an Impure Protein Fraction

In one exemplary embodiment of the practice of this invention, the starting material for providing the impure protein fraction comprising Factor VIII complex is cryoprecipitate. The cryoprecipitate is recovered from human blood plasma that has been collected and tested according to procedures approved by the U.S. Food and Drug Administration. The plasma is frozen at a temperature of about −20° C., and is subsequently thawed at 0° C. to 5° C. During the thawing process, a precipitate forms (the "cryoprecipitate") which is removed by centrifugation and recovered for further purification and concentration.

The cryoprecipitate is dissolved in a heparin solution which comprises distilled water and from about 30 to 150 units of heparin per ml of water at a pH of about 6.0 to about 8.5. In an exemplary embodiment, 110 units of heparin per ml of water at a pH of 7.5 is used. The solution is then mixed at a temperature of from about 15° C. to about 35° C. until the cryoprecipitate is completely dissolved (approximately 10 minutes), to provide a heparin solution containing impure Factor VIII complex. Preferably, the temperature during mixing is maintained at about 30° C. and the volume of heparin solution used is from about 2 to about 10 liters per kilogram of cryoprecipitate, and most preferably, 3 liters of solution per kilogram of cryoprecipitate. After the cryoprecipitate is dissolved the pH of the solution is adjusted to about 6.9 to about 7.1 using, for example, 0.1M HCl, and the solution is stirred for an additional 20 to 30 minutes.

One unit of heparin is defined to mean one U.S.P. (United States Pharmacopoeia) unit. The U.S.P. unit of heparin is that quantity required to prevent 1.0 ml of citrated sheep plasma from clotting for one hour after the addition of 0.2 ml of a 1:100 calcium chloride ($CaCl_2$) solution. The term "heparin" as used herein is meant to include heparin itself and the pharmaceutically acceptable, water soluble salts of heparin, e.g., the sodium salts. A suitable example of a commercially available heparin sodium product is U.S.P. heparin from Lyphomed Company, of Melrose Park, Ill., or from Sigma Chemical Company (Sigma No. H7005), of St. Louis, Mo.

Polyethylene glycol, preferably having a molecular weight in the range of from about 2000 to about 6000 (more preferably, from about 3000 to about to about 4000 and most preferably 3350) is then added to the impure Factor VIII complex solution to provide a PEG solution having a final PEG concentration of from about 1% to about 5% (wt/vol). PEG can be obtained from Dow Chemical Corporation. The term "% (wt/vol)" as used herein means the weight of material in grams added per 100 ml of starting volume of solution. The percentages referred to herein are all weight per 100 ml volume unless otherwise indicated. Preferably, the PEG is added in the form of a solution prepared by dissolving the PEG in distilled water which comprises a citrate salt (such as sodium citrate). In one exemplary embodiment, the aqueous PEG solution added to the impure Factor VIII complex solution, comprises about 30% (wt/vol) PEG, 0.21% (wt/vol) sodium citrate dihydrate, and 0.08% (wt/vol) citric acid monohydrate at a pH of 6.2. The pH of the PEG solution is adjusted to between 5.5 and 7.1 with an acid such as dilute acetic acid. In one exemplary embodiment, the pH is adjusted to about 6.3. The pH adjusted PEG solution is mixed for at least 15 minutes at a temperature of from 15° C. to 35° C.

The addition of 1% (wt/vol) to 5% (wt/vol) PEG, preferably 3% (wt/vol) to 5% (wt/vol), and most preferably 3.5% (wt/vol) to form the PEG solution results in precipitation of various proteins including fibronectin and fibrinogen but leaves the Factor VIII complex in solution. The PEG precipitate is separated from the impure Factor VIII complex solution (the PEG supernatant) by centrifugation. The PEG supernatant is recovered and is then clarified by filtration by being filtered through a 2.0 µm filter and then through a 0.5 µm filter. The PEG supernatant is now ready for further processing and purification of Factor VIII complex by use of an anion exchange chromatography resin.

In an exemplary embodiment of practice of this invention, the Factor VIII complex production process includes steps for inactivating viruses that may be present in such blood products, e.g., hepatitis B virus, hepatitis C virus, HIV (AIDS virus), Cytomegalovirus, Epstein-Barr virus, and the like, prior to the affinity chromatography step. In one embodiment, a solution comprising both an organic solvent and a detergent is added to the PEG supernatant to inactivate virus that may be present. The amount of organic solvent and detergent added preferably results in a solution comprising about 0.3% (wt/vol) organic solvent and about 1% (wt/vol) detergent. A detergent useful in practice of principles of the invention is one sold by under the trademark "TWEEN-80" by Fisher Scientific, of Springfield, N.J.; another is a detergent sold under the trademark "TRITON X-100," by Aldrich Company, of Milwaukee, Wis. Useful organic solvents are tri-n-butyl-phosphate (TNBP), ethyl ether, and the like. The solution is incubated for about 6 hours to about 7 hours at a temperature of from about 24° C. to about 30° C. Inactivation of virus using organic solvent/detergent mixture is described in U.S. Pat. No. 4,540,573, which issued on Sep. 10, 1985 to Neurath et al., and which is incorporated herein by reference.

Preparation of the Anion Exchange Chromatography Column

In one embodiment of the invention, chromatographic columns such as those supplied by Amicon Corporation of Danvers, Mass. are used. Other columns from other manufacturers could also be used. Many different sized columns can be used, the three most common column sizes used to practice the present invention are: column volume 5 ml/ø 1.0 cm×6.4 cm; column volume 50 ml/ø 2.5 cm×10.2 cm; and column volume of 150 ml/ø 4.5 cm×9. An anion exchange resin is packed into the column. The preferred chromatography resin is QAE550 C Registered TM, a quaternary amine resin coated onto a polymer matrix, manufactured by TosoHaas of Montgomeryville, Pa. The resin is packed into the column following the manufacturer's instructions contained in the publication entitled "TosoHaas—Bioseparation Specialists—Toyopearl® Chromatographic Resins," which is hereby incorporated by reference. The resin inside the column is then washed with 3 column volumes of deionized water and 3 column volumes of 2M NaCl, 0.025M histidine, at a pH of 6.8. The term "column volume" means the volume of the resin in the column, i.e. 5 ml for the 5 ml column, 50 ml for the 50 ml column, and 150 ml for the 150 ml column. The resin is then equilibrated with a buffer comprising 0.35M NaCl, 0.025M histidine at a pH of 6.8.

Separation of Factor VIII Complex by Anion Exchange Chromatography

The Impure Factor VIII complex rich sample (PEG supernatant) is applied to a 5.0 ml column containing the anion exchange resin at a flow rate of about 1 ml/min., to a 50 ml column containing the anion exchange resin at a flow rate of about 9.0 ml/min. and to the 150 ml column at a flow rate of about 20 ml/min. using a binding buffer comprising 0.35M NaCl, 0.025M histidine at a pH of 6.8. The three columns are then washed with three column volumes of 0.35M NaCl, 0.025M histidine, pH 6.8, and three column volumes of 0.1M CaCl$_2$, 0.025M histidine, pH 6.8 to remove any unbound protein. Bound Factor VIII is then eluted with 3 to 5 column volumes of an elution buffer comprising from about 0.14M to about 0.2M CaCl$_2$, about 0.025M histidine, at a pH of about 6.8. The chromatography is performed at room temperature.

Purification of Factor VIII Complex by Glycine/NaCl Precipitation

The Factor VIII complex in the eluate is precipitated by the addition of glycine and NaCl. The addition of glycine and NaCl is an effective means of increasing the specific activity of the Factor VIII complex. However, it is important that this step be included after the anion exchange chromatography step, or other suitable partial purification step, since its inclusion at an earlier step results in a "milky" solution thereby causing the precipitation of undesirable components from the solution in addition to the Factor VIII complex.

The eluate fractions recovered from the anion exchange chromatography medium are first brought to about 1.5M to about 2.5M glycine and then brought to about 1.2M to about 3M NaCl. The solution is mixed at about 15° C. to about 25° C. for about two hours and the precipitate formed is collected by centrifugation. Preferably, glycine and NaCl are added to the fractions until the solution had a final concentration of about 2M glycine and about 1.6M NaCl.

The precipitate, which contains Factor VIII complex, is washed with a wash solution comprising about 0.025M histidine, pH 6.8, 2M glycine, and 1.3M NaCl, and is collected by centrifugation. The wash procedure results in the resolubilization of contaminating proteins caught in the glycine/NaCl precipitate but not the Factor VIII complex. The wash procedure can be repeated, if desired, and the final precipitate collected by centrifugation or filtration and dissolved in a buffer comprising about 0.025M histidine, 0.1M arginine, pH 6.0 to 8.0.

Figure 2A:
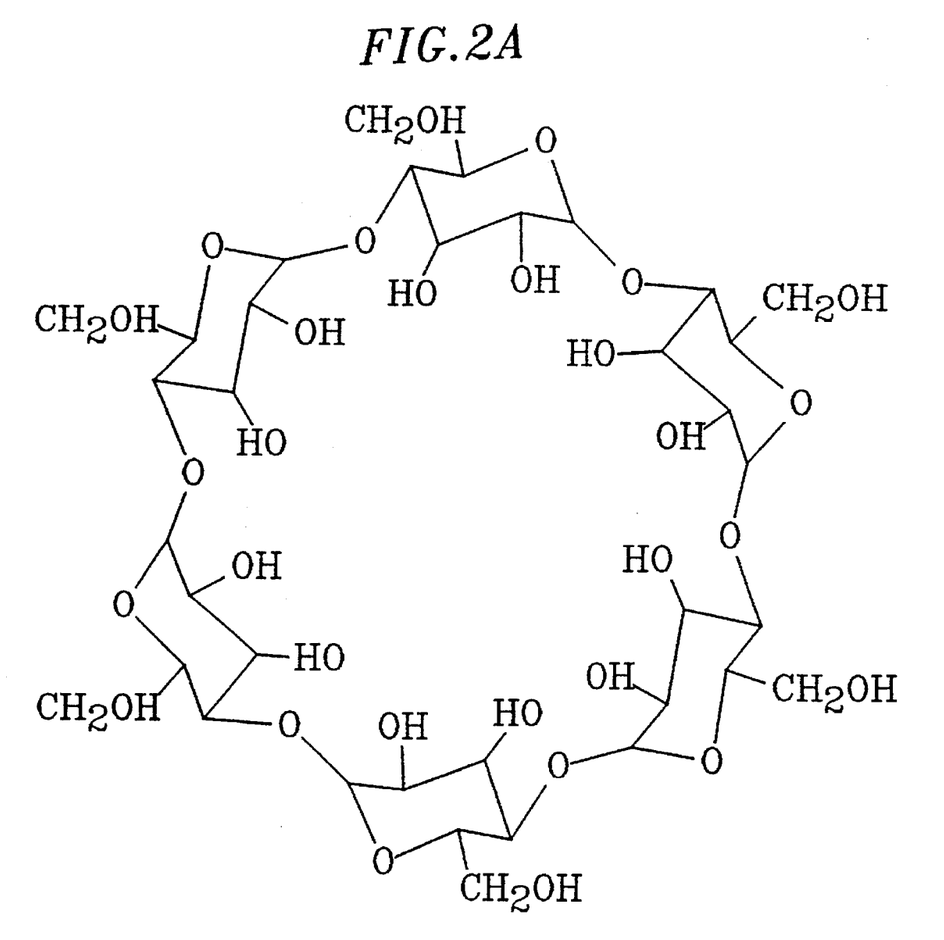
FIG. 2A is a schematic illustrating the structure of α-cyclodextrin.
Figure 2B:
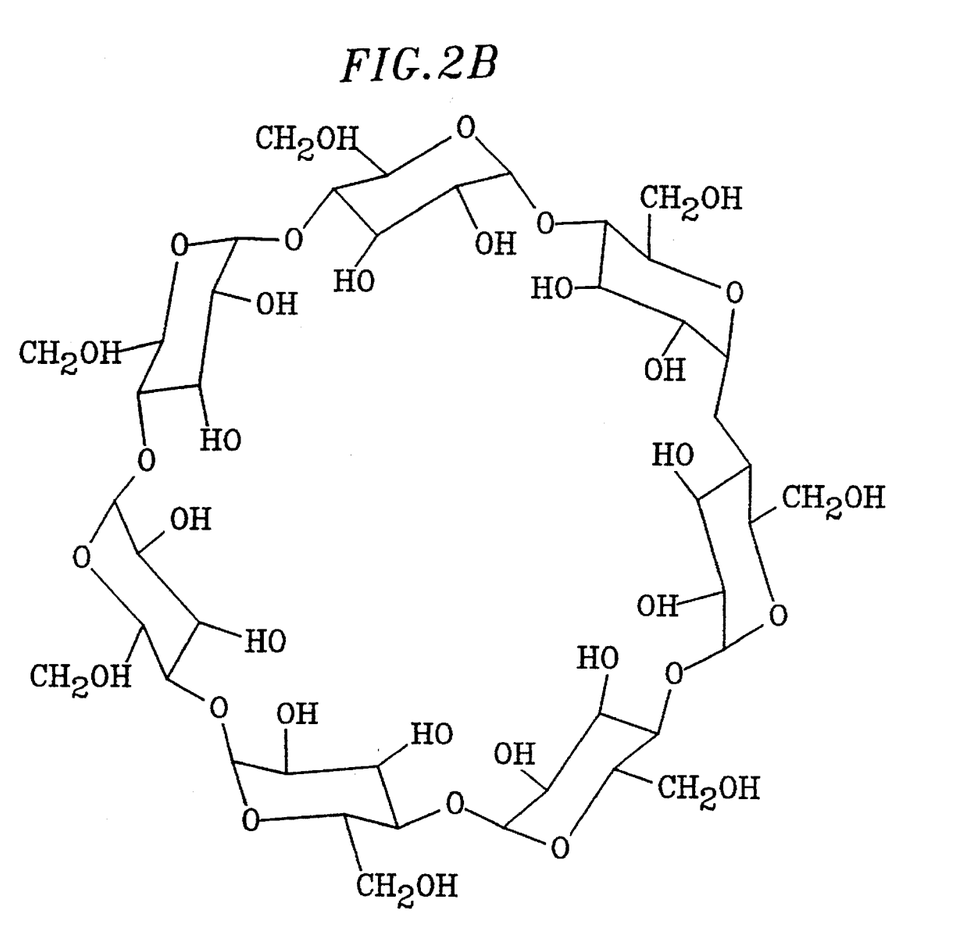
FIG. 2B is a schematic illustrating the structure of β-cyclodextrin.
Figure 2C:
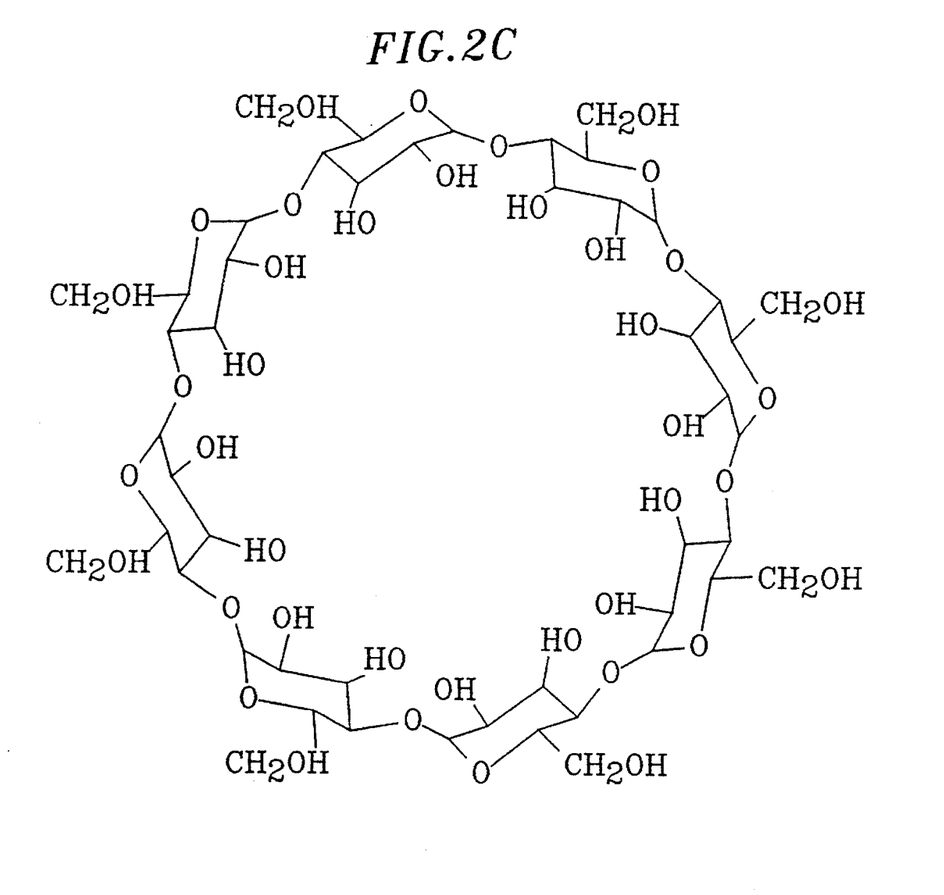
FIG. 2C is a schematic illustrating the structure of γ-cyclodextrin.

After the precipitate is dissolved, cyclodextrins are added as a stabilizer to the Factor VIII solution. Cyclodextrins are a group of homologous oligosaccharides that are obtained from starch by the action of enzymes from *Bacillus macerans*. They are cyclic molecules containing six or more α-D-glucopyranose units linked together at the 1, 4 positions as in amylose. The cyclic structure may also be referred to as a torus. FIGS. 2A, 2B, and 2C illustrate the structure of the three most common cyclodextrins. α-Cyclodextrin has six glucopyranose units, β-cyclodextrin has seven glucopyranose units, and γ-cyclodextrin has eight glucopyranose units. Mixtures of these materials are included in the term cyclodextrin as used herein.

Cyclodextrins are added to the solution to obtain a final concentration of 3% (wt/vol). Cyclodextrins are available from American Maize-Products Co., Hammond, Ind. under the trade name Cavitron Cyclo-Dextrins™. The purified Factor VIII solution containing cyclodextrins as a stabilizer is referred to as "purified bulk."

The purified bulk is then introduced into vials, with each vial containing a desired number of units of Factor VIII activity. The solutions are then lyophilized to provide separate vials of purified Factor VIII complex concentrate.

The lyophilized product is treated again to deactivate viruses that may be in the Factor VIII complex product. Viral deactivation is performed by dry heating the lyophilized product in an oven at 80° C. for 72 hours.

The final product is now available for shipping to treating physicians and hospitals.

EXAMPLE 1

Preparation of an Impure Protein Fraction Containing Factor VIII

Four kilograms of cryoprecipitate was dissolved in 12 liters of distilled water containing about 110 units of heparin per ml of water. The heparin solution was mixed at a temperature of about 30° C. until the cryoprecipitate was completely dissolved (approximately 10 minutes), to provide an impure protein fraction of Factor VIII in a heparin solution. After the cryoprecipitate was dissolved, the pH of the solution was adjusted to about 7.0 using 0.1M HCl and the solution was stirred for an additional 20 to 30 minutes.

An aqueous PEG solution comprising about 31.5% (wt/vol) PEG-3350, 0.22% (wt/vol) sodium citrate dihydrate, and 0.08% (wt/vol) citric acid monohydrate, at a pH of 6.2, was then added to the cryoprecipitate solution to give a final concentration of 3.5% (wt/vol) PEG. The pH of the impure Factor VIII complex, PEG and heparin solution was adjusted to about 6.3 with dilute acetic acid. The pH adjusted solution was mixed for approximately 15 minutes at a temperature of about 27° C. The addition of PEG resulted in precipitation of various contaminating proteins from the Factor VIII complex which remained in solution.

The PEG precipitate was separated from the Factor VIII complex containing supernatant solution by centrifugation. The supernatant containing the impure Factor VIII complex was recovered. The supernatant was then filtered through a 2.0 μm filter and then through a 0.5 μm filter. The supernatant was then treated to inactivate viruses which may be present by adding a solution of tri-n-butyl-phosphate and TWEEN-80 until the solution contained a final concentration of about 0.3% (wt/vol) tri-n-butyl-phosphate and about 1% (wt/vol) TWEEN-80 The solution was then incubated at 25° C. for about 6 hours.

The viral inactivated supernatant solution, i.e., the viral-inactivated Factor VIII complex containing impure protein fraction, was clarified by filtration, and was then recovered for use in further purification steps. At this stage, 20 kg of Factor VIII containing solution was present.

The Factor VIII activity in the PEG supernatant was tested. The Factor VIII yield was about 280 units/kg of plasma. Factor VIII procoagulant activity was measured with one stage Activated Partial Thromboplastin Time (APTT) using a substrate, Factor VIII deficient plasma, with Universal Coagulation Reference Plasma (UCRP) as a standard. The standard and the samples were diluted with buffer containing 0.1M NaCl and 0.025M histidine at a pH of 6.8 and 1% human albumin. Coagulation times were then measured with an automatic coagulometer, Coag-A-Mate®, using calcium chloride to initiate clot formation and determine the clotting time in seconds.

EXAMPLE 2

Ionic Strength for Binding Factor VIII to the Anion Exchange Chromatography Column PEG supernatant from example 1 was tested for its Factor VIII activity. The Factor VIII activity of the PEG supernatant was arbitrarily designated as 100%. The Factor VIII was applied to the TosoHaas QAE-550C column using a buffer that was 0.15M NaCl, 0.025M histidine, pH 6.8.

Various ionic concentrations of NaCl buffer (0.15M, 0.25M, 0.35M and 1.0M) were then applied to the column to test for the optimum ionic strength of the binding buffer. The effluents were collected and the Factor VIII activity was measured as described above. The NaCl buffers used also included 0.025M histidine and were all at a pH of 6.8.

The results are shown in Table I. Total protein was measured using a spectrophotometer and measuring the absorption at $A_{280}$. 95% or more of the Factor VIII complex bound to the column when the concentration of NaCl was 0.35M or less, and greater than 95% of the $A_{280}$, impurity proteins, passed through the column. This result demonstrated that the optimum ionic strength of the NaCl buffer for binding Factor VIII was 0.35M or less.

TABLE I

| Ionic Strength for Binding Factor VIII | | | |
|---|---|---|---|
| Fraction | F. VIII (units) | Activity (%) | Protein (Total $A_{280}$) |
| PEG-sup (applied) | 82.7 | 100 | 155 |
| 0.15M NaCl fraction | <4 | <5 | 127 |
| 0.25M NaCl fraction | <4 | <5 | 11 |
| 0.35M NaCl fraction | 4 | 5 | 11 |
| 1.0M NaCl fraction | 81.8 | 99 | 2 |

EXAMPLE 3

Binding Capacity of the Anion Exchange Column

Figure 3:
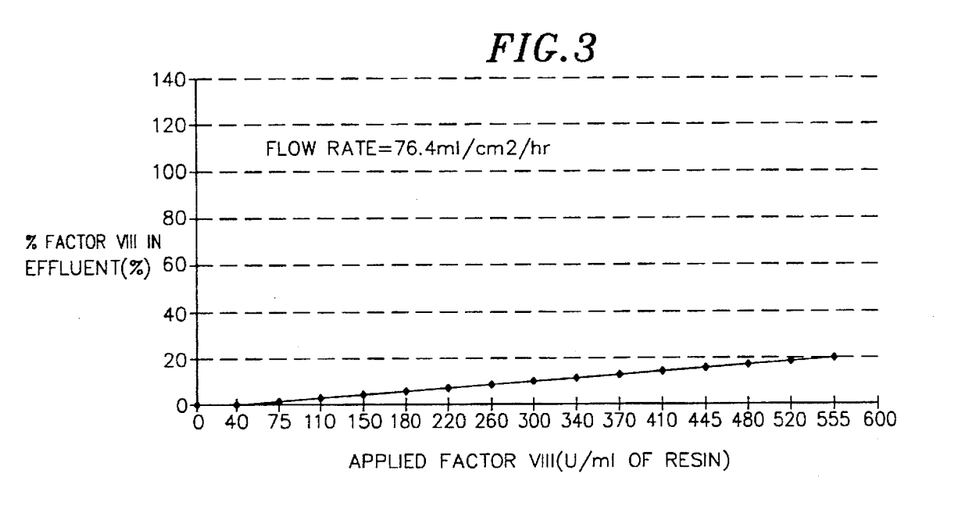
FIG. 3 is a line graph illustrating the binding capacity of the QAE-550C resin to bind Factor VIII.

PEG supernatant samples from example 1 having varying amounts of Factor VIII activity ranging from 0 U/ml to more than 500 U/ml of QAE resin were placed in a buffer comprising 0.35M NaCl and 0.025M histidine at a pH of 6.8 and were loaded into a 5 ml anion exchange column at a flow rate of 76.4 ml/cm²/hr to find the maximum binding capacity of the QAE-550C resin. The factor VIII activity of the effluents from the column were measured as described above and compared to the original Factor VIII activity in the PEG supernatant samples. The % of Factor VIII activity lost in the effluent was graphed against the amount of Factor VIII (U/ml) applied to the column. The results, which are demonstrated in FIG. 3, show that more than 80% of applied Factor VIII bound to the resin. The QAE-550C binding capacity was found to be at least 500 Units of Factor VIII/ml of QAE resin.

EXAMPLE 4

Elution with NaCl

The PEG supernatant obtained from example 1 was applied to the QAE-550C column using a buffer comprising 0.35M NaCl and 0.025M histidine at a pH of 6.8. The column was washed with three column volumes of a buffer comprising 0.35M NaCl and 0.025M histidine at a pH of 6.8 solution. Elution of the Factor VIII was carried out using an elution buffer comprising 1.0M NaCl and 0.025M histidine at a pH of 6.8. As can be seen by the results in Table II, greater than 95% of the bound Factor VIII was eluted with 1.0M NaCl, and a 420 fold purification was achieved by a single step of QAE-550C column chromatography. Rec. stands for recovery. S.A. stands for the specific activity of Factor VIII (units/mg protein) which is the Factor VIII activity (units/ml) divided by the protein concentration (mg/ml) of the solution.

TABLE II

| Ionic Strength for Binding Factor VIII | | | | |
|---|---|---|---|---|
| Sample | Volume ml | U/ml | F. VIII Total U | Rec. % | S.A. U/mg of protein |
| Applied (PEG Supernatant) | 245 | 3.6 | 882 | 100 | 0.7 |
| Column Effluent | 152 | 0.2 | 30 | 3 | — |
| Column Wash | 110 | 0.3 | 33 | 4 | — |
| Column Eluant | 74 | 11.8 | 873 | 99 | 295 |

EXAMPLE 5

Stability of Factor VIII Eluted with NaCl

Figure 4:
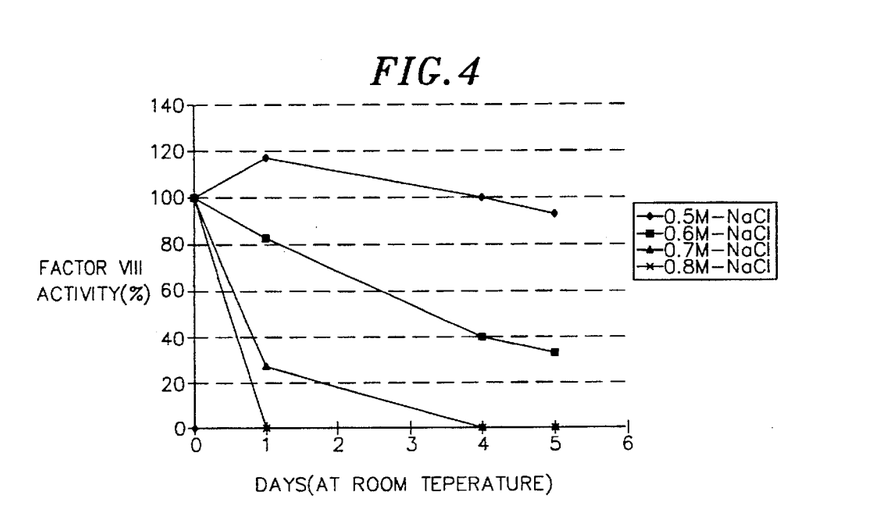
FIG. 4 is a line graph illustrating the stability of the Factor VIII eluted with NaCl.

The stability of the Factor VIII in the eluate was tested. PEG supernatant from Example 1 was added to six different QAE-550C columns using a binding buffer comprising 0.35M NaCl and 0.025M histidine at a pH of 6.8. A different concentration of NaCl (0.5M, 0.6M, 0.7M, 0.8M, 0.9M, or 1.0M) was used to elute Factor VIII from each one of the six columns. The eluting buffers also contained 0.025M histidine and were all at a pH of 6.8. The eluates were collected and each eluate was diluted with 0.025M histidine pH 6.8 buffer to adjust the ionic strength of the eluate to 0.25M NaCl in order to match physiological conditions. The solutions were stored at room temperature and the Factor VIII activity was measured as described above. The Factor VIII activity was measured at day 0, day 1, day 4, and day 5. The results of the elution with NaCl concentrations of 0.5, 0.6, 0.7, and 0.8M are shown in FIG. 4.

The degree of stability of the eluate was found to be dependent on the ionic strength of the elution buffer. The column eluates at higher ionic strengths (greater than 0.6M NaCl) were found to be less stable than the lower ionic strength eluates. Column eluates of 0.8M NaCl or greater were not stable for even one day. The most likely reason for the instability of Factor VIII was the presence of an inactivating factor in the column elute at higher ionic strengths.

EXAMPLE 6

Testing for the Presence of an Inactivating Factor

Figure 5:
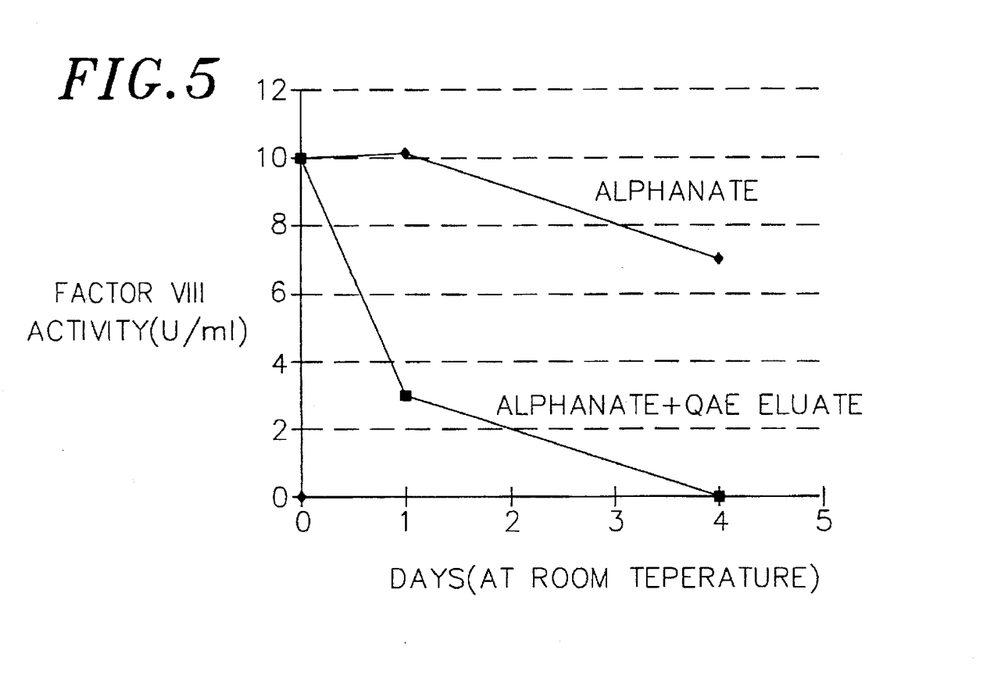
FIG. 5 is a line graph illustrating the stability of a known stable Factor VIII product with and without the eluate of the QAE-550C column using 1.0M NaCl elution buffer.

The eluate from example 5 eluted with 1M NaCl was mixed with a known stable Factor VIII product, Alphanate™, to test for the presence of an inactivating factor in the eluate. The eluate was diluted to 10 U of Factor VIII activity/ml with a 0.025M histidine buffer at a pH of 6.8. The diluted eluate was then added to diluted Alphanate™ (10 U of Factor VIII/ml). This mixture was stored at room temperature and tested for stability over a 5 day period. Factor VIII activity of the mixture was found to be unstable (see FIG. 5). This result indicated the existence of an inactivating factor in the eluate which destroyed the Factor VIII activity of Alphahate™.

EXAMPLE 7

Elution with NaCl or $CaCl_2$

Figure 6:
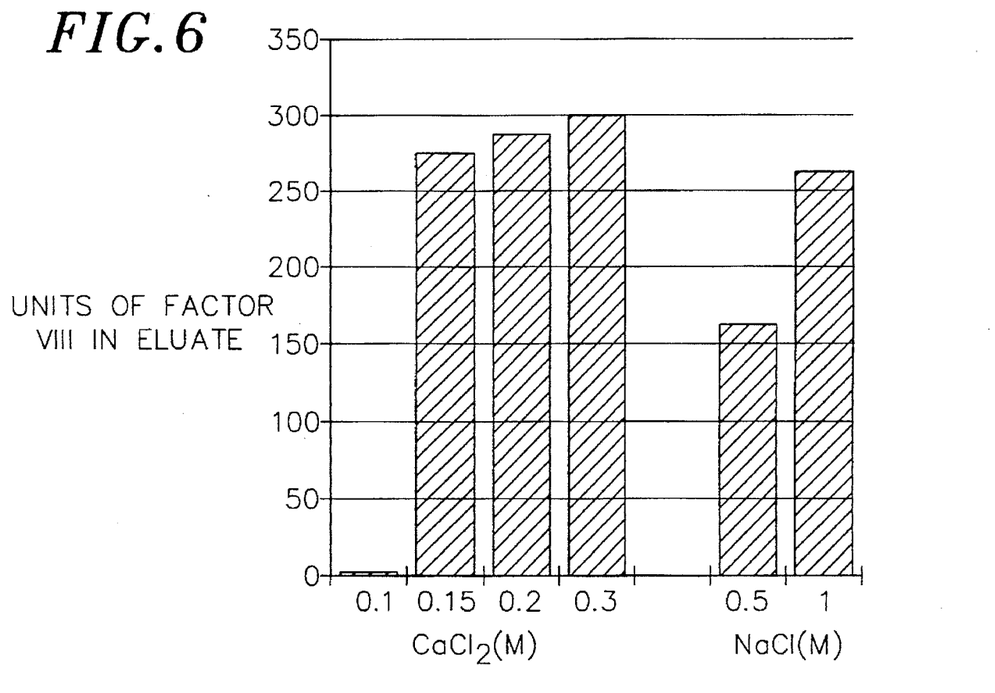
FIG. 6 is a bar graph comparing the elution efficiency of NaCl elution buffers with $CaCl_2$ elution buffers.

Since the sodium chloride eluted an inactivating factor along with the Factor VIII complex, various concentrations of sodium chloride and calcium chloride buffers were evaluated for optimal elution of Factor VIII complex (see FIG. 6). The PEG supernatant of example 1 was loaded into an anion exchange QAE-550C column using a binding buffer comprising 0.35M NaCl and 0.025M histidine at a pH of 6.8. The column was eluted with varying amounts of NaCl and $CaCl_2$ elution buffers containing 0.025M histidine at a pH of 6.8. The varying buffers had different ionic strengths (for the NaCl buffers, 0.5M had the ionic strength of 43.7 mS and 1.0 M had the ionic strength of 93.1 mS; for the $CaCl_2$ buffers, 0.1M had the ionic strength of 17.2 mS, 0.15M had the ionic strength of 22.0 mS, 0.2M had the ionic strength of 26.4 mS, and 0.3M had the ionic strength of 36.1 mS). Calcium chloride proved to be more effective for Factor VIII complex elution than sodium chloride even with the lower ionic strengths.

EXAMPLE 8

Elution with Varying Concentrations of $CaCl_2$

Figure 7:
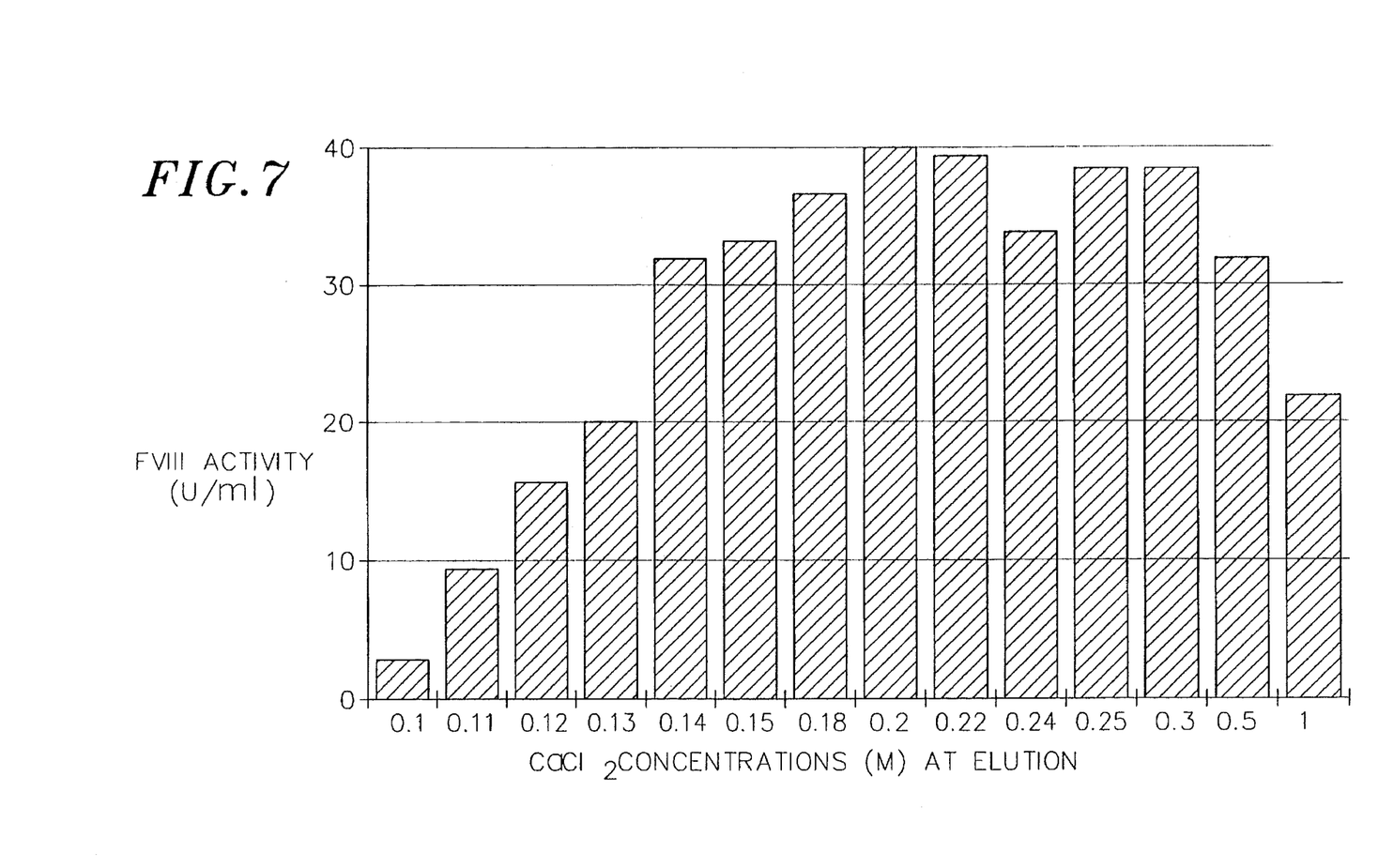
FIG. 7 is a bar graph comparing the Factor VIII activity as a function of the concentration of $CaCl_2$ in the elution buffer.

Factor VIII from example 1 was loaded into the anion exchange column with a binding buffer comprising 0.35M NaCl and 0.025M histidine at a pH of 6.8. The QAE-550C resin in the column was then subdivided into 14 equal lengths and washed with 0.35M NaCl, 0.025M histidine buffer at a pH of 6.8. The 14 columns were eluted with different concentrations of $CaCl_2$ ranging from 0.1M to 1M. Each eluting buffer had a concentration of histidine of 0.025M and was at a pH of 6.8. The Factor VIII activity was measured as described above. The results are shown in FIG. 7. The amount of Factor VIII activity in the eluate steadily increased as the concentration of $CaCl_2$ increased from 0.1M to 0.2M. In the concentration range of 0.14M to 0.5M the amount of Factor VIII eluted ranged from about 33 U/ml to about 40 U/ml. From this data it was determined that the concentration of $CaCl_2$ in the elution buffer should be about 0.14M or greater.

EXAMPLE 9

Stability of Factor VIII Eluted with $CaCl_2$

Figure 8:
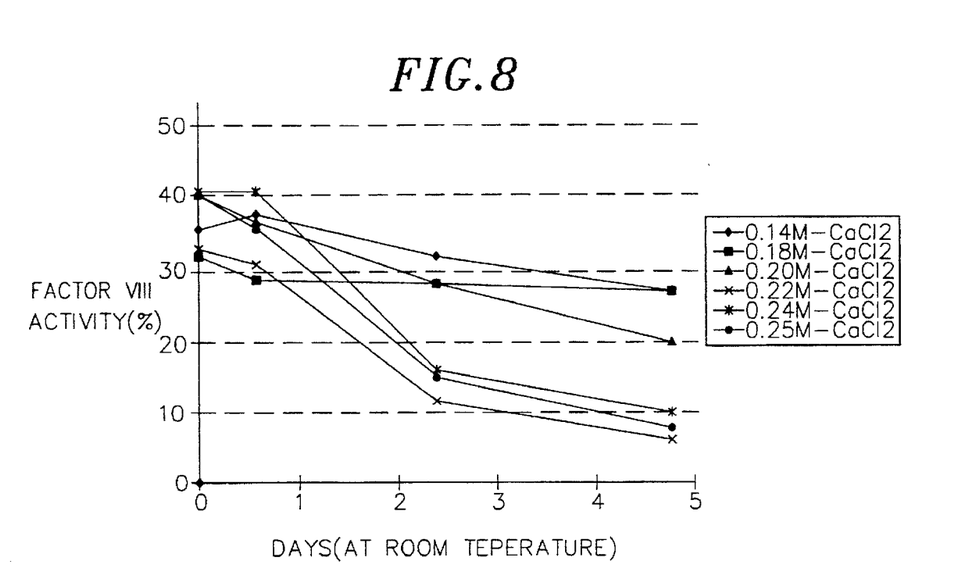
FIG. 8 is a line graph illustrating the stability of the Factor VIII eluted with varying concentrations of $CaCl_2$ in the elution buffer.

Each of the Factor VIII containing eluants from example 8 were tested for the stability of the Factor VIII complex. Each sample was adjusted to a $CaCl_2$ concentration of 0.01M using a buffer of 0.025M histidine at a pH of 6.8 and the Factor VIII activity was measured. The initial Factor VIII activity for each sample was designated 100%. The Factor VIII activity was then measured at 5 hours, 24 hours, and 48 hours. The results are shown in FIG. 8 for the elution buffers with the concentration of $CaCl_2$ ranging from 0.14M to 0.25M. Factor VIII eluted with $CaCl_2$ in a concentration below 0.2M demonstrated the best stability. Factor VIII eluted with a concentration of $CaCl_2$ greater than 0.2M demonstrated the worst stability. Factor VIII eluted with 0.2M $CaCl_2$ demonstrated intermediate stability.

Based on the results of examples 8 and 9, Factor VIII elution should be carried out with a $CaCl_2$ solution in the range of about 0.14M to about 0.2M. Although not known for a certainty, it is believed that an inactivating factor is eluted with the Factor VIII when the concentration of $CaCl_2$ is greater than about 0.2M.

EXAMPLE 10

Elution with 0.2M $CaCl_2$

After taking all the above chromatography conditions into account, an experiment was conducted using a 5 ml column packed with a QAE-550C resin and an elution buffer comprising 0.2M $CaCl_2$ and 0.025M histidine at a pH of 6.8. The results are presented in table III.

TABLE III

| | Ionic Strength for Binding Factor VIII | | | | |
|---|---|---|---|---|---|
| Sample | Volume ml | U/ml | F. VIII Total U | Rec. % | S.A. U/mg of protein |
| Applied (PEG Supernatant) | 500 | 2.9 | 1450 | 100 | 0.7 |
| Column Effluent | 792 | 0.5 | 396 | 27 | — |
| Column Wash | 72 | <0.1 | <7 | <0.5 | — |
| Column Eluant | 40 | 25.7 | 1028 | 71 | 204 |

EXAMPLE 11

Glycine and NaCl Fractionation

The glycine and sodium chloride fractionation which was described in U.S. Pat. No. 5,288,853 and is hereby incorporated by reference, was evaluated for a further purification and concentration step. From the Factor VIII eluted with 0.2M CaCl$_2$ and 0.025M histidine as described in example 9, glycine was added to the eluate to a final concentration of 2M and then NaCl was added to a final concentration of 1.6M. The mixture was then incubated for 2 hours at room temperature. The mixture was then centrifuged and the Factor VIII recovered in the precipitate demonstrated a step yield of 80%. The result is shown in Table IV. The final recovery of Factor VIII was 76% from PEG-supernatant which is equivalent to 213 U/kg of plasma. The specific activity was 466 U/mg of protein.

TABLE IV

Preparation of Factor VIII Complex

| Sample | Volume ml | U/ml | F. VIII Total U | % | S.A. U/mg of protein |
|---|---|---|---|---|---|
| Applied (PEG-sup) | 4,450 | 3.0 | 13,350 | 100 | 0.5 |
| Column effluent | 6,827 | 0.2 | 1,365 | 10 | — |
| Column eluate | 435 | 29.0 | 12,615 | 94 | 112 |
| NaCl precipitate | 87 | 116.0 | 10,092 | 76 | 466 |

EXAMPLE 12

Preparation of Factor VIII Bulk

Factor VIII PEG supernatant from example 1 was loaded into an anion exchange chromatography column with a binding buffer comprising 0.35M NaCl and 0.025M histidine at a pH of 6.8. The column was washed with a washing buffer comprising 0.35M NaCl and 0.025M histidine at a pH of 6.8 and then washed again with a washing buffer comprising 0.1M CaCl$_2$ and 0.025M histidine at a pH of 6.8. The Factor VIII complex was eluted with an elution buffer comprising 0.2M CaCl$_2$ and 0.025M histidine at a pH of 6.8. The Factor VIII complex was then further purified using glycine and NaCl to precipitate out Factor VIII complex as described in example 11. The Factor VIII complex precipitate was reconstituted in a solution of 0.1M arginine and 0.025M histidine at a pH of 7.3. This solution is also referred to as "purified bulk." The Factor VIII activity in the bulk solution was measured and this solution was then used for further processing.

In one instance, starting from 4 kg of cryoprecipitate, 20 kg of viral deactivated PEG supernatant was obtained. After the anion exchange chromatography, 527 ml of Factor VIII complex solution was obtained. Finally, 165 ml of purified Factor VIII complex bulk solution was obtained after glycine and NaCl precipitation.

EXAMPLE 13

Cyclodextrin as a Stabilizer

In this example, the sterile Factor VIII bulk solution from the process of example 12 with the specific activity of 333 units per milligram was filled into vials with various additives and then lyophilized. The lyophilized Factor VIII product was then subjected to dry-heating (80° C. for 72 hours). The final preparations were reconstituted with water for injection. Reconstitution time and residual Factor VIII activity were recorded. The results of the tests, which are set forth in Table V below, show that Factor VIII which was lyophilized from the solution comprising 3% (wt/vol) cyclodextrin (hydroxy propyl-β-cyclodextrin) was more stable than the Factor VIII prepared using various amounts of other materials, such as Tween 80, PEG, glycine, sodium citrate, dextrin, and histidine.

TABLE V

Screening of Additive for Highly Purified Factor VIII

| | F. VIII: U/ml | | Recon. time (sec) | Cake appearance |
|---|---|---|---|---|
| Additive | Before DH | After DH | after DH | after DH |
| No additive | 77.5 (100%) | 45.1 (58%) | 20 | + |
| 0.1% Tween 80 | 71.8 (100%) | 18.4 (26%) | 12 | ++ |
| 0.1% PEG | 83.2 (100%) | 13.8 (17%) | >10 min | + |
| .2M glycine | 78.8 (100%) | 42.1 (53%) | 15 | + |
| 0.2M Na citrate | 92.8 (100%) | 26.1 (28%) | 60 | + |
| 3% cyclodextrin | 75.8 (100%) | 74.5 (98%) | <10 | +++++ |
| 3% dextrin | 79.2 (100%) | 43.1 (54%) | 22 | ++++ |
| 0.1M histidine | 70.9 (100%) | 51.0 (72%) | 10 | +++ |

EXAMPLE 14

Cyclodextrin Stabilization

In a similar experiment as example 13, to the bulk prepared in example 12, a control and a test solution using 3% cyclodextrin as an additive were prepared. The solutions were lyophilized and lyophilized samples were then subjected to dry-heating at 80° C. for 72 hours. Activities of Factor VIII (F.VIII:C), Ristocetin Cofactor (R. CoF.) and vWF (vWF:Ag) were tested before and after dry heating.

The results of the tests are shown in Table VI below. It appears that Factor VIII associated with 3% cyclodextrin was substantially more stable when dry-heated.

TABLE VI

Activity of the Product in Dry-Heating Step

| Additive | Dry heating (80° C., 72 hr) | F. VIII:C. U/ml (%) | R. Cof. U/ml | vWF:Ag U/ml |
|---|---|---|---|---|
| No additive | before DH | 132 (100) | 20 | 31 |
| | after DH | 86 (65) | 21 | 32 |
| 3%-cyclodextrin (HPB) | before DH | 127 (100) | 25 | 44 |
| | after DH | 114 (90) | 22 | 43 |

EXAMPLE 15

Stabilization with Different Cyclodextrins

In another test, Factor VIII bulk from example 12 was stabilized with three different cyclodextrins, namely, hydroxy propyl-β-cyclodextrin at 3% (wt/vol), methyl ether-β-cyclodextrin at 3% (wt/vol), and γ-cyclodextrin at 3% (wt/vol). Results of this test, which are set forth below in Table VII, show that each of the three different cyclodextrin used were effective in stabilizing Factor VIII.

TABLE VII

| Additive 2 | Dry heating (80° C., 72 hr) | F. VIII:C U/ml (%) |
|---|---|---|
| 3% hydroxy propyl-β-cyclodextrin (HPB) | before DH | 58 (100) |
| | after DH | 52 (90) |
| 3% methyl ether-β-cyclodextrin | before DH | 68 (100) |
| | after DH | 69 (101) |
| 3% γ-cyclodextrin | before DH | 54 (100) |
| | after DH | 61 (113) |

EXAMPLE 16

Stabilization with Varying Concentrations of Cyclodextrin

In another test, purified bulk Factor VIII was lyophilized with various concentrations of hydroxy propyl-β-cyclodextrin and dry-heated at 80° C. for 72 hours. The products were then reconstituted and the Factor VIII activity was measured and compared to the original Factor VIII activity of the sample. The results are demonstrated in FIG. 9.

Figure 9:
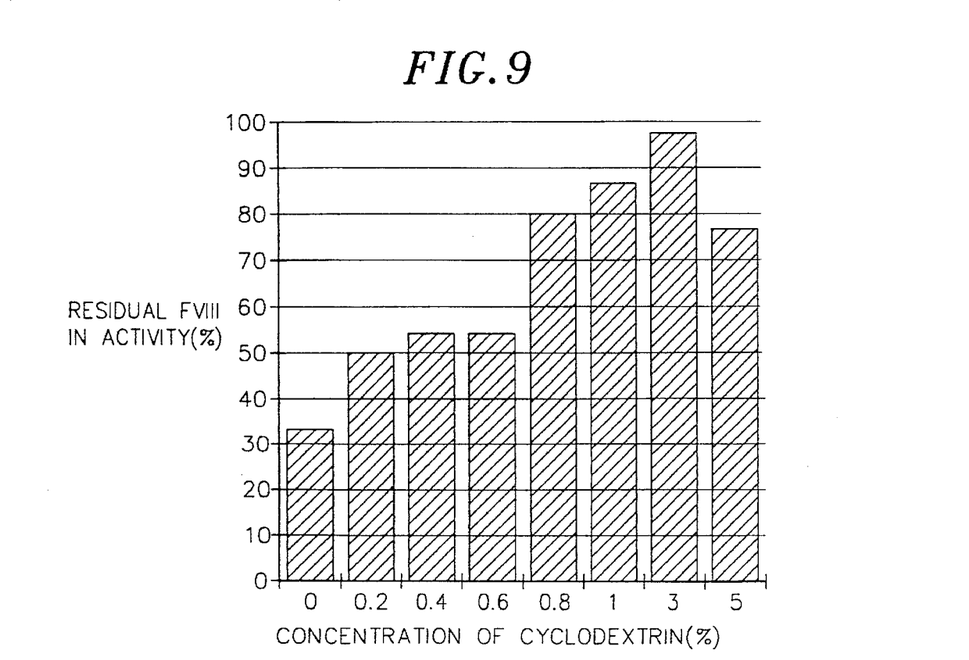
FIG. 9 is a bar graph comparing the residual Factor VIII activity as a function of concentration of hydroxy propyl β-cyclodextrin for stabilization during the dry heating step.

As shown, optimal stabilization occurred in concentration levels of cyclodextrin ranging from 0.8 to 3% (wt/vol). At a cyclodextrin concentration of 5% (wt/vol), the Factor VIII activity showed a slight decrease compared to the cyclodextrin concentration of 0.8 to 3% (wt/vol). This test demonstrates that the most likely useful concentration of cyclodextrin to be used as a stabilizer and to help in the reconstitution of Factor VIII is in a concentration ranging from about 1% to about 3% (wt/vol).

The preferred embodiment has been detailed above. The preferred embodiment has many advantages including more than a 4000 fold purification (a ratio of specific activity from the starting material stage to the final bulk), which is a 20 fold increase in purity over the method described in U.S. Pat. No. 5,288,853. The new process utilizes an anion exchange resin with an extremely high binding capacity, greater than 500 U/ml of gel. Under the new process, a dual virus inactivation method is employed for safety involving the use of an organic solvent and detergent (OSD, 1.0% Tween-80/ 03% (wt/vol) TNBP) and terminal dry heating at 80° C. for 72 hours. Furthermore, cyclodextrin was used as a stabilizer to maintain the high specific activity of the final Factor VIII product. The New Factor VIII method features: higher yield, smaller resin volume for manufacturing (5–10 L), and a higher specific activity in the final product.

Thus, a process for purifying Factor VIII complex is disclosed which allows for high yields of Factor VIII in an inexpensive process. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A process for separating Factor VIII complex (a complex of Factor VIII:C and vWF) from an impure protein fraction containing Factor VIII complex, the process comprising the steps of:

(a) providing an aqueous solution of an impure protein fraction containing Factor VIII complex;

(b) applying the impure protein fraction solution to an anion exchange chromatographic medium to thereby bind Factor VIII complex to the anion exchange medium;

(c) eluting Factor VIII complex from the anion exchange medium using an eluting buffer comprising from about 0.10M to about 0.20M $CaCl_2$; and (d) recovering Factor VIII complex eluted from the column.

2. The process of claim 1 wherein the $CaCl_2$ present in the eluting buffer is at a concentration ranging from about 0.14M to about 0.2M.

3. The process of claim 2 wherein the $CaCl_2$ present in the eluting buffer is at a concentration of 0.2M.

4. The process of claim 1 wherein the eluting buffer further comprises histidine at a concentration of from about 0.015M to about 0.035M.

5. The process of claim 4 wherein the concentration of histidine in the eluting buffer is 0.025M.

6. The process of claim 1 wherein the eluting buffer has a pH from about 6.0 to about 8.0.

7. The process of claim 6 wherein the pH of the eluting buffer is maintained at about 6.8.

8. The process of claim 1 wherein the anion exchange chromatography medium comprises a quaternary amino ethyl resin.

9. The process of claim 8 wherein the resin is a QAE-550C resin manufactured by TosoHaas.

10. The process of claim 1 wherein the aqueous solution of an impure protein fraction containing Factor VIII complex is derived from cryoprecipitate.

11. A process for separating Factor VIII complex (a complex of Factor VIII:C and vWF) from an impure protein fraction containing Factor VIII complex, the process comprising the steps of:

(a) providing an aqueous solution of an impure protein fraction containing Factor VIII complex;

(b) applying the impure protein fraction solution to an anion exchange chromatographic medium located in a column to thereby bind Factor VIII complex to the anion exchange medium;

(c) eluting Factor VIII complex from the anion exchange medium using an eluting buffer comprising from about 0.10M to about 0.20M $CaCl_2$;

(d) recovering Factor VIII complex eluted from the column;

(e) adding glycine and NaCl to the recovered eluate to thereby precipitate Factor VIII complex; and (f) recovering Factor VIII precipitated complex.

12. The process of claim 11 wherein the $CaCl_2$ present in the eluting buffer is at a concentration ranging from about 0.14M to about 0.2M.

13. The process of claim 12 wherein the $CaCl_2$ present in the eluting buffer is at a concentration of 0.2M.

14. The process of claim 11 wherein the eluting buffer further comprises histidine at a concentration of from about 0.015M to about 0.035M.

15. The process of claim 14 wherein the concentration of histidine in the eluting buffer is 0.025M.

16. The process of claim 11 wherein the eluting buffer has a pH from about 6.0 to about 8.0.

17. The process of claim 16 wherein the pH of the eluting buffer is maintained at about 6.8.

18. The process of claim 11 wherein the anion exchange chromatography medium comprises a quaternary amino ethyl resin.

19. The process of claim 18 wherein the resin is a QAE-550C resin provided by TosoHaas.

20. The process of claim 11 wherein the aqueous solution of an impure protein fraction containing Factor VIII complex is derived from cryoprecipitate.

21. The process of claim 11 wherein the Factor VIII complex is precipitated with about 1.5M to about 2.5M glycine and about 1.2M to about 3.0M NaCl.

22. The process of claim 21 wherein the Factor VIII complex is precipitated with about 2M glycine and about 1.6M NaCl.

23. A process for separating Factor VIII complex (a complex of Factor VIII:C and vWF) from cryoprecipitate, comprising the steps of:

(a) dissolving the cryoprecipitate in a heparin solution;

(b) adding polyethylene glycol to the dissolved cryoprecipitate to precipitate proteins other than Factor VIII complex;

(c) separating the polyethylene glycol supernatant from the precipitate;

(d) treating the recovered supernatant with an organic solvent and a detergent to deactivate viruses;

(e) applying the viral deactivated supernatant to an anion exchange chromatographic medium containing a quaternary amino ethyl group located in a column to thereby bind Factor VIII complex to the anion exchange medium;

(f) eluting Factor VIII complex from the anion exchange medium using an eluting buffer comprising from about 0.10M to about 0.20M $CaCl_2$ and about 0.025M histidine at a pH of 6.8;

(g) recovering Factor VIII complex eluted from the column;

(h) adding glycine and NaCl to the recovered eluate to a final concentration of 2.0M glycine and 1.6M NaCl to thereby precipitate Factor VIII complex;

(i) recovering Factor VIII precipitated complex;

(j) reconstituting Factor VIII complex in a solution comprising 0.1M arginine, 0.025M histidine, 3% (wt/vol) cyclodextrin at a pH of 7.3;

(k) lyophilizing the reconstituted Factor VIII complex; and (l) dry heating the lyophilized Factor VIII complex at 80° C. for 72 hours.

* * * * *

UNITED STATES PATENT AND TRADEMARK OFFICE
CERTIFICATE OF CORRECTION

PATENT NO. : 5,659,017
DATED : August 19, 1997
INVENTOR(S) : Prabir Bhattacharya; Toshiharu Motokubota;
Norman M. Fedalizo It is certified that error appears in the above-indentified patent and that said Letters Patent is hereby corrected as shown below:

Column 1, lines 47,56, change "Alphahate™" to -- Alphanate™ --.
Column 4, line 23, replace "3000 to about to about 4000"with
   -- 3000 to about 4000 --.
Column 5, line 1, after "sold" delete "by".
Column 7, line 18, replace "TWEEN-80 The" with -- TWEEN-80. The --.
Column 9, line 39, change "Alphahate™" to -- Alphanate™ --.

Signed and Sealed this

Twenty-third Day of February, 1999

*Attest:*

Q. TODD DICKINSON

*Attesting Officer*  Acting Commissioner of Patents and Trademarks